United States Patent
Deckert et al.

(10) Patent No.: US 6,472,554 B1
(45) Date of Patent: Oct. 29, 2002

(54) CONTINUOUS PREPARATION OF ALKYL ESTERS OF (METH) ACRYLIC ACID

(75) Inventors: Petra Deckert, Wiesloch (DE); Holger Herbst, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/619,574

(22) Filed: Jul. 19, 2000

(30) Foreign Application Priority Data

Jul. 28, 1999 (DE) .......................... 199 35 453

(51) Int. Cl.$^7$ ............................. C07C 69/52
(52) U.S. Cl. ....................................... 560/205
(58) Field of Search ......................... 560/205

(56) References Cited

U.S. PATENT DOCUMENTS

| | | | | |
|---|---|---|---|---|
| 4,250,328 A | * | 2/1981 | Fujita et al. | 560/205 |
| 4,329,492 A | * | 5/1982 | Andoh et al. | 560/205 |
| 4,435,594 A | * | 3/1984 | Matsumura et al. | 560/205 |
| 4,733,004 A | * | 3/1988 | Pascoe | 560/205 |
| 4,739,108 A | * | 4/1988 | Lillwitz | 560/205 |
| 5,386,052 A | * | 1/1995 | Sakakura | 560/205 |

FOREIGN PATENT DOCUMENTS

| | | | |
|---|---|---|---|
| CA | 2196917 | * | 8/1997 |
| DE | 198 14 449 | | 10/1999 |
| DE | 198 51 983 | | 5/2000 |

* cited by examiner

*Primary Examiner*—Alan L. Rotman
*Assistant Examiner*—Taylor V. Oh
(74) *Attorney, Agent, or Firm*—Oblon, Spivak, McClelland, Maier & Neustadt, P.C.

(57) ABSTRACT

A process for the continuous preparation of acrylates of (meth)acrylic acid by reaction of (meth)acrylic acid with alkanols of 4 to 8 carbon atoms in an esterification zone is proposed, in which the reaction mixture removed from the esterification zone is first fed to a three-stage prepurification and then worked up by rectification for isolating the desired ester.

14 Claims, No Drawings

CONTINUOUS PREPARATION OF ALKYL ESTERS OF (METH) ACRYLIC ACID

The present invention relates to a process for the continuous preparation of alkyl esters of (meth)acrylic acid by reacting (meth)acrylic acid with alkanols of 4 to 8 carbon atoms in a reaction zone, the reaction mixture containing the desired ester being removed from the reaction zone by the liquid phase method, purified beforehand and then worked up by rectification. The present invention furthermore relates to an apparatus and a use of the process.

The term (meth)acrylic is used predominantly as abbreviated notation for acrylic and/or methacrylic.

Alkyl esters of (meth)acrylic acid are generally known and are important, for example, as reactive monoethylenically unsaturated monomers for the preparation of aqueous polymer dispersions by free radical aqueous emulsion polymerization, which polymer dispersions are used, for example, as adhesives.

Usually, the preparation of the alkyl (meth)acrylate is carried out by direct, acid-catalyzed reaction (esterification) of (meth)acrylic acid with the corresponding alkanols.

One route for the industrial production of (meth)acrylic acid is the catalytic gas-phase oxidation of suitable $C_3$-/$C_4$-precursors (for example propylene, acrolein, isobutene or methacrolein) with molecular oxygen. However, this procedure gives not pure (meth)acrylic acid but a gas mixture, i.e. crude (meth)acrylic acid which, in addition to (meth)acrylic acid, contains, amongst other substances, acetic acid as a byproduct, the separation of which from (meth)acrylic acid, particularly by rectification, is expensive (cf. for example DE-A 198 14 449).

Processes in which this crude (meth)acrylic acid is esterified directly by reaction with alkanols and the removal of the byproduct is thus transferred from the acid level to the ester level have therefore been proposed. Such a process is described, for example, in the non-prior-published German Patent Application 198 51 983. According to this, crude (meth)acrylic acid is reacted with alkanols of 1 to 8 carbon atoms in a phase free of solvents, at elevated temperatures and in the presence of a strongly acidic esterification catalyst in a reaction zone, the water formed during a residence time in the reaction zone and being part of a mixture comprising starting alkanol is separated from the reaction mixture by rectification in a rectification unit RI attached to the reaction zone, the reaction mixture containing the desired ester is removed from the reaction zone and first prepurified, the acid esterification catalyst being separated off preferably by washing with water and this separation being completed preferably by subsequent washing with an aqueous alkali metal-hydroxide solution, and finally, in further rectification units, the desired ester is separated from the prepurified reaction mixture by rectification.

It is an object of the present invention to provide an improved process for the continuous preparation of alkyl esters of (meth)acrylic acid by reacting (meth)acrylic acid with alkanols of 4 to 8 carbon atoms, which ensures higher availability of the plant, an improvement in the yield and a reduction of the amount of residue.

We have found that this object is achieved by a process for the continuous preparation of alkyl esters of (meth) acrylic acid by reacting (meth)acrylic acid with alkanols of 4 to 8 carbon atoms in a phase free of solvents, at elevated temperatures and in the presence of a strongly acidic esterification catalyst, in which the (meth)acrylic acid, the alkanol and the esterification catalyst are fed to a reaction zone, the water formed during a residence time in the reaction zone and being part of a mixture comprising starting alkanol is separated from the reaction mixture in a first rectification unit RI attached to the reaction zone, the distillate obtained is separated into an organic phase containing a starting alkanol and into an aqueous phase containing water, the organic phase is recycled to the rectification unit RI, the reaction mixture containing the desired ester and removed from the reaction zone is fed to a prepurification, 1. in a first prepurification stage, the predominant part of the esterification catalyst being separated off by extraction by means of washing with water and
2. in a second prepurification stage, the strongly acidic components being neutralized and extracted with an aqueous alkali solution by reactive extraction, the remaining organic reaction mixture I is passed into a further separation zone comprising rectification units and the resulting alkyl ester of (meth)acrylic acid is isolated therein.

In said process, the prepurification comprises a third stage in which
3. residual salts and aqueous foreign-phase fractions are removed by extraction with water from the organic reaction mixture I remaining after the second prepurification stage, before it is passed on into the separation zone comprising further rectification units.

It was surprisingly found that, in the process according to the non-prior-published German Patent Application 198 51 983, the prepurification of the reaction mixture containing the desired ester is decisively improved by a further, third prepurification stage, by means of which the downstream separation of the desired ester from the residual reaction mixture by rectification is improved in terms of economy and ecology.

A particularly suitable starting material for the esterification is a (meth)acrylic acid which was produced by catalytic gas-phase oxidation of the $C_3$-/$C_4$-precursors stated at the outset with molecular oxygen. The crude (meth)acrylic acid obtained in this manner can preferably be fed directly to the esterification, but it is just as possible to use any more highly purified (meth)acrylic acid as the acid starting material. Crude (meth)acrylic acid contains as impurities in particular up to 5% by weight of acetic acid and in addition frequently up to 1% by weight of maleic acid and/or the anhydride thereof and low molecular weight aldehydes, frequently in an amount of up to 0.5% by weight, and up to 0.5% by weight of other components, for example propionic acid, diacrylic acid and polymerization inhibitors, for example phenothiazine. The (meth)acrylic acid content of the crude (meth)acrylic acid which can preferably be used is frequently at least 95, often at least 97 or at least 98 or at least 99,% by weight.

Suitable alkanol starting materials are in principle all alkanols of 4 to 8 carbon atoms, n-butanol and 2-ethylhexanol being particularly preferred.

Suitable strongly acidic esterification catalysts for the novel process are in particular strong mineral acids, preferably sulfuric acid, but also strong organic acids, in particular sulfonic acids, such as methanesulfonic acid, benzenesulfonic acid, dodecanesulfonic acid, para-toluenesulfonic acid or mixtures of some or all of the abovementioned acids.

The esterification is carried out in the manner described in DE 198 51 983, in a reaction zone which may consist of one or more reaction regions. In one embodiment of the invention, comprising a plurality of reaction regions, it is advantageous to cascade them. The liquid discharge stream of one reaction region expediently forms the feed of the downstream reaction region. This can be effected in a simple manner with the aid of an overflow or by means of pumps.

Where the individual reaction regions are apparatus separated from one another, the number thereof is expediently ≧2 and ≦4, taking into account the capital costs. If more than one reaction region is set up within one and the same reactor (for example by the use of separating plates), the number of reaction regions may also be greater than 4. In the case of a plurality of reaction regions, the vapors of the individual reaction regions can be fed to a common rectification unit RI, for example a common rectification column, whose liquid discharge is expediently fed to the first reaction region. According to the invention, however, it may be expedient to attach one rectification unit RI to each of a plurality of reaction regions, if required to all, and to recycle its liquid reflux into one or more reaction regions, expediently into those to which the rectification units are attached. Frequently, no rectification unit RI is attached to the first reaction region.

The term rectification unit RI is to be understood here as well as below as being the general designation for apparatuses in which vapors produced by supplying heat ascend and are in contact with downward-flowing liquid phase. As a rule, they are rectification columns which contain internals for thorough contact between liquid and vapor. Dual-flow trays and/or structured packing are preferably used as internals in all rectification units.

As a rule, the esterification is operated in a known manner in the reaction zone at reduced pressure (i.e. <1 bar), which facilitates the removal of the water of reaction by rectification via the rectification unit RI. However, it can also be carried out at atmospheric pressure (i.e. at 1 bar) or at superatmospheric pressure. Usually, the reaction zone having the attached rectification unit RI is separate from the other rectification units, both spatially and with regard to control. The conditions in the reaction region and in the rectification units used for isolating the desired ester can therefore be adjusted in a very flexible manner. Usually, the reaction pressure in the reaction regions is from 100 mbar to ≦1 bar, frequently from 100 to 800 mbar, often from 500 to 700 mbar.

The temperature of the reaction mixture in the reaction regions usually corresponds to the set pressure and to the composition of the reaction mixture present in the reaction region. In the case of cascading (with a plurality of reaction regions), this means that the reaction temperature generally increases along the cascade (the reaction pressure is usually kept constant along the cascade).

The temperature in the reaction zone is as a rule from 70 to 160° C. It is usually from 70 to 150° C., preferably from 80 to 130° C., in the first reaction region and from 100 to 160° C., preferably from 110 to 130° C., in the last reaction region. In the case of n-butanol, it is expedient to choose the reaction temperature in all regions within from ≧100° C. to ≦140° C., i.e. to allow said temperature to increase from ≧100° C. in the first reaction region to ≦140° C. in the last reaction region.

The total residence time of the reactants in the reaction zone is preferably established so that a minimum conversion of 90, preferably of 99,% by weight, based on (meth)acrylic acid, is achieved; this corresponds as a rule to 0.25 to 15 hours, frequently 1 to 7 or 2 to 5 hours. In successive reaction regions, the residence time of the reactants usually decreases.

The content of strongly acidic esterification catalyst in the reaction zone is expediently from 0.1 to 20, frequently from 0.5 to 5,% by weight, based on the reaction mixture contained therein, of $H_2SO_4$, or an equivalent (usually equimolar) amount of organic sulfonic acid and/or sulfuric acid.

The distillate obtained in the rectification unit RI, usually at the top of a rectification column, is separated into an organic and into an aqueous phase by cooling during condensation (alternatively, phase separation by rectification is also suitable). The organic phase comprises predominantly organic components (mainly alkanol, alkyl acetate, alkyl (meth)acrylate and dialkyl ether), while the aqueous phase comprises predominantly water of esterification. As a rule, none of the aqueous phase is recycled to the rectification unit RI, especially in the preparation of n-butyl acrylate. Rather, it is usually separated off. If required, the small amounts of alkanol present in solution in the aqueous phase can be separated off in an alkanol stripping column by stripping, for example by means of steam or air, and recycled to the reaction zone, usually to the first reaction region. Recycling of a part of the aqueous phase to the rectification unit RI is usually effected only when the distillate separated off in the rectification unit RI would contain (meth)acrylic acid (in significant amounts) without such recycling.

According to the invention, the aqueous phase separated off, the process water from the esterification reaction, is preferably added as an extracting agent, in the first and/or third prepurification stage, to the reaction mixture removed from the reaction zone. By using alkanol-containing, for example butanol-containing, in particular butanol-saturated process water, the transfer of the alkanol, for example butanol, in the prepurification stages from the organic to the aqueous phase is avoided.

The amount of organic phase recycled to the rectification unit RI is as a rule such that the reflux ratio (the ratio of recycled amount to amount removed) is from 5 to 40, preferably from 10 to 30. Overall, the separating efficiency in the rectification unit RI is frequently chosen so that the alkyl acetate content of the organic phase removed is at least 5, as a rule at least 10, often at least 20,% by weight.

Before the alkyl acetate-containing organic phase removed is disposed of, for example incinerated, it can be subjected to an extraction with water for increasing the yield, in order to separate off alkanol, e.g. n-butanol, contained therein and transfer it to the aqueous phase. The aqueous phase containing alkanol, e.g. n-butanol, can likewise be fed to the abovementioned alkanol stripping column and the alkanol separated off therein recycled to the reaction zone in this way. The water freed from alkanol in the alkanol stripping column can be disposed of as wastewater requiring treatment and/or can be reused for the extraction.

Alternatively, the alkyl acetate-containing organic phase removed could also be worked up by rectification to give a top product comprising mainly alkyl acetate and alkanol and a bottom mixture comprising mainly alkyl (meth)acrylate and alkanol. The bottom mixture could be recycled directly to the reaction zone and the top product either subjected to thermal treatment or worked up as follows:

Extraction of the alkanol with water and recovery by stripping of the alkanol, for example with steam, or by rectification and recycling of said alkanol to the reaction zone;

Hydrolysis with aqueous alkali solution and subsequent separation of the alkanol from the aqueous phase by stripping or rectification and recycling of the alkanol to the reaction zone;

The above hydrolysis could also be carried out directly with the alkyl acetate-containing purge stream.

In the case of an esterification of 2-ethylhexanol, the alkyl acetate-containing organic phase removed is expediently simultaneously a purge for octene formed as byproduct (dehydration of 2-ethylhexanol).

As a rule, both the (meth)acrylic acid (usually stabilized at from 200 to 1000 ppm by weight of polymerization inhibitor, as a rule phenothiazine) and the strongly acidic esterification catalyst are fed directly to the reaction zone (spatially separately and/or together). The starting alkanol to be esterified is preferably fed to the reaction zone via the rectification unit RI attached to said reaction zone. However, it would of course also be possible to feed the starting alkanol directly to the reaction zone.

The rectification unit RI may consist of one or more rectification columns of known design, in particular having dual-flow trays or structured packings or sieve trays. Usually, it is supplemented by associated condensers and separation vessels. The reaction regions may consist, for example, of reactors having natural-circulation or forced-circulation evaporators, i.e. the thorough mixing of the reaction mixture can be effected by stirring, circulation by means of a pump and/or natural circulation. The heat is supplied in a manner known per se, for example by double-jacket heating or external and/or internal heat exchangers.

To stabilize the rectification unit RI to undesired formation of polymer initiated by free radicals, a solution of a polymerization inhibitor is expediently added to the top of said rectification unit. A suitable solvent in this context is, for example, the alkyl (meth)acrylate which is the desired product or the organic phase of the distillate separated off in the rectification unit RII, which organic phase is to be recycled to the rectification unit RI. A preferably used polymerization inhibitor is phenothiazine.

The condensers (for example, plate-type or tube-bundle condensers) in which the vapors ascending in the rectification unit RI are condensed for recovering the distillate to be separated off in the rectification unit RI are expediently likewise stabilized by means of polymerization inhibitors known per se. For this purpose, an aqueous solution (about 0.1–1% strength by weight) of at least one inhibitor (as a rule having a water solubility of at least 1% by weight (25° C., 1 bar)) is advantageously fed to the condenser and/or added to the condensate. Examples of suitable such water-soluble inhibitors are hydroquinone, p-nitrosophenol, phenylenediamines, such as Kerobit BPD (N,N'-diisobutyl-p-phenylenediamine), p-nitrosodiethylaniline, 2,2,6,6-tetramethylpiperidin-N-oxyl, 4-hydroxy-2,2,6,6-tetramethylpiperidin-N-oxyl or mixtures of the abovementioned members. Particularly in the case of a preparation of n-butyl acrylate, an aqueous solution which contains 4-hydroxy-2,2,6,6-tetramethylpiperidin-N-oxyl (preferably as the sole inhibitor) is preferably used.

Before the discharge from the reaction zone, essentially comprising as a rule desired ester, unconverted (meth)acrylic acid, byproducts having lower boiling points than the desired ester, such as alkyl acetate or dialkyl ether, strongly acidic esterification catalyst, higher-boiling oxyesters formed by Michael addition and polymerization inhibitor, is fed to the further separation zone comprising rectification zones, the predominant part of the strongly acidic esterification catalyst is first separated from the reactor discharge in a first prepurification stage.

This can be done in detail in various ways.

In the case of strong mineral acids, e.g. sulfuric acid, and/or organic sulfonic acids, this separation can be effected in a particularly simple manner known per se, for example by washing the esterification discharge with water. The resulting aqueous phase containing strongly acidic esterification catalyst and unconverted (meth)acrylic acid and any process polymerization inhibitor can be expediently recycled directly to the reaction zone, disposed of and/or combined with the alkaline aqueous phase mentioned in the next section, for the purpose of back-extraction. The demand for fresh, strongly acidic esterification catalyst is reduced by circulation. High-boiling components which are soluble in water are also circulated, in particular maleic anhydride; in order to reduce or to avoid soiling of the apparatuses, in particular of the heat exchangers, as a result of the increase in the concentration of high boilers, a part-stream of said aqueous phase, preferably about 5, particularly preferably about 10,% by weight of the aqueous phase, is thus advantageously removed from the circulation. It was found that the degree of soiling of the heat exchangers, measured in terms of the maximum operating time after which operation had to be stopped owing to insufficient introduction of heat, can be reduced by a factor of 4 by removing a part-stream of about 10% by weight of the aqueous phase, compared with complete recycling thereof to the esterification.

The organic phase from the first prepurification stage, which, in addition to the desired ester, contains in particular the starting alkanol, (meth)acrylic acid and alkyl sulfate, is fed to a second prepurification stage, in which the strongly acidic components are neutralized and extracted by reactive extractions by means of an aqueous alkali solution. The alkali solution used as extracting agent is preferably an aqueous sodium hydroxide and/or potassium hydroxide solution, preferably in a concentration of from 1 to 50, particularly preferably from 6 to 15,% by weight. It is very particularly advantageous to use a 6% strength by weight sodium hydroxide solution. The amount of added aqueous sodium hydroxide solution is monitored by pH measurement and depends on the equivalence point of the sodium acrylate.

The mixture thus obtained runs off into a phase separator, where the aqueous phase which contains about 10% by weight of sodium acrylate settles. By acidification, in particular with sulfuric acid, particularly preferably with the aqueous part-stream removed in the first prepurification stage, acrylic acid is liberated and is extracted in a counter-current column with essentially alkanol, for example n-butanol. The resulting extract containing acrylic acid is recycled to the esterification in the reaction zone. The wastewater is fed to a wastewater treatment plant after stripping of the alkanol, for example of the n-butanol.

The lighter, organic phase, which still contains from about 0.5 to 15, in particular from 1 to 10,% by weight of foreign phase fractions, i.e. aqueous phase fractions, is fed to a third prepurification stage, in which, according to the invention, residual salts, in particular sodium salts of acrylic acid and of sulfuric acid, and aqueous foreign-phase fractions are removed according to the invention by extraction with water.

For this purpose, the organic phase removed from the second prepurification stage is thoroughly mixed with water, preferably with alkanol-saturated, in particular butanol-saturated, water and is separated in a further phase separator into a lighter organic phase and a heavier aqueous phase.

The residual organic reaction mixture I remaining from the second prepurification stage is mixed with water, according to the invention, preferably in a stirred kettle which may be equipped in principle with a stirrer type of any desired design.

Particularly preferably, the stirred kettle is equipped with a single-stage or multistage impeller stirrer.

Advantageously, in the third prepurification stage, from 0.05 to 1, preferably from 0.1 to 0.5, particularly preferably 0.2, part by weight of water is added to the residual organic reaction mixture I per part by weight of organic phase.

Preferably, the water added in the third prepurification stage can be acidified beforehand, in particular in such a way that the aqueous phase has a pH of ≦6, preferably from 3 to 6, after the extraction.

The stirred kettle is preferably designed in a manner such that the power introduced by the stirrer is from 0.1 to 2, preferably from 0.5 to 1, particularly preferably 0.8, kW/m$^3$.

Preferably, a residence time of from 0.5 to 60, in particular from 10 to 30, more preferably 20, min is established in the stirred kettle. The mixture obtained in particular in the stirred kettle is passed into a further phase separator, where it separates into a heavier aqueous phase and a lighter organic phase. The aqueous phase can advantageously be used for diluting the alkali solution to be used in the second prepurification stage. Residual sodium acrylate still present in the aqueous phase can be recovered by extraction (acidification and subsequent countercurrent extraction with alkanol) and can be recycled to the esterification.

The lighter organic phase is then fed for working up by rectification to obtain the desired ester, in particular in the manner described in the unpublished German Patent Application 198 51 983.

For carrying out the first and/or third prepurification stage, according to the invention an apparatus in the form of a mixer-settler arrangement is preferably used, the mixer being in the form of a tube filled with loose packings or internals. This ensures particularly thorough mixing of the phases.

The Examples which follow illustrate the invention.

COMPARATIVE EXAMPLE

In a production plant for continuous preparation of butyl acrylate, consisting of a reactor cascade comprising three reactors with external circulation evaporators and attached distillation columns for separating off the water of esterification, butyl acrylate was synthesized from acrylic acid and butanol using sulfuric acid as a catalyst. The temperatures in the reaction stills were 115, 118 and 120° C. A constant pressure of 500 mbar was maintained. The ratio of butanol to acrylic acid was 1.2 kg/kg. The sulfuric acid was adjusted so that a constant concentration of 1.5% by weight was maintained at the exit of esterification still 3. The residence time in the synthesis stage was 2 hours. The reaction discharge was fed to a first prepurification stage, the major part of the sulfuric acid being separated from the reaction discharge by continuous extraction with 0.5% by weight of water in a mixer-settler apparatus consisting of a static mixer in the form of a W-shaped tubular reactor (V=0.45 m$^3$) filled with Pall rings and a phase separator (V=10 m$^3$). The organic phase from the phase separator was fed to a second prepurification stage, and was neutralized in an apparatus designed analogously to the first prepurification stage comprising mixer-settler and phase separator, by adding 6% strength by weight NaOH solution. The lighter, organic phase still had residual amounts of from 150 to 4000 ppm of sodium. The operation of the downstream purification by distillation had to be limited as a rule to 7 to 10 days since the sodium salt compounds were precipitated under the distillation conditions and constricted the column cross-section. Shutdown and subsequent cleaning with water were necessary. The plant availability was thus reduced.

EXAMPLE 1

Water (0.2% by weight) was added to the organic phase from the second prepurification stage (corresponding to the Comparative Example), having a residual Na content of from 150 to 500 ppm, at room temperature in a 1 l stirred vessel, at a pH of 6, and mixing was carried out at different speeds. After the stirrer had been switched off, the phases separated after a short time, and the analysis of the organic phase gave Na values of 1 ppm. Table 1 shows the Na values of the crude butyl acrylate before and after the extraction with water (third prepurification stage).

TABLE 1

| Speed l/min | Power introduced kW/m$^3$ | Stirring time min | Na before extraction ppm | Na after extraction ppm |
|---|---|---|---|---|
| 440 | 0.8 | 10 | 481 | 1 |
| 400 | 0.8 | 20 | 306 | 1 |

EXAMPLE 2

Water (0.2% by weight) was added to the same product as that described in Example 1, at room temperature in a 100 l stirred vessel, at a pH of 6, and mixing was carried out at different speeds. After the stirrer had been switched off, the phases separated after a short time, and the analysis of the organic phase gave Na values of 2 ppm. Table 2 shows the Na values of the crude butyl acrylate before the extraction with water (third prepurification stage):

TABLE 2

| Speed l/min | Power introduced kW/m$^3$ | Stirring time min | Na before extraction ppm | Na after extraction ppm |
|---|---|---|---|---|
| 130 | 0.3 | 20 | 362 | 2 |
| 180 | 0.8 | 20 | 306 | 2 |
| 180 | 0.8 | 80 | 306 | 2 |
| 310 | 4.1 | 20 | 177 | 2 |

The availability of the plants for the distillative purification of the products according to Examples 1 and 2 was not impaired by soiling.

We claim:

1. A process for the continuous preparation of alkyl esters of (meth)acrylic acid by reacting (meth)acrylic acid with alkanols of 4 to 8 carbon atoms in a phase free of solvents, at elevated temperatures and in the presence of a strongly acidic esterification catalyst, comprising feeding the (meth)acrylic acid, the alkanol and the esterification catalyst into a reaction zone in which water is formed during a residence time of the reactants in the reaction zone and being part of a mixture comprising starting alkanol which is separated from the reaction mixture in a first rectification unit rI attached to the reaction zone, separating the distillate obtained into an organic phase containing a starting alkanol and into an aqueous phase containing water, recycling the organic phase to the rectification unit RI, and feeding the reaction mixture containing the desired ester, which is removed from the reaction zone, to a prepurification process comprising:
   1. in a first prepurification stage, extracting the reaction mixture obtained by washing with water, thereby removing most of said esterification catalyst from the reaction mixture, and
   2. in a second prepurification stage, neutralizing and extracting the strongly acidic components with an aqueous alkali solution by reactive extraction of the reaction mixture from stage I;

passing the remaining reaction mixture as reaction mixture I into a further separation zone comprising rectification units and isolating the resulting alkyl ester of (meth)acrylic acid therein, wherein the prepurification comprises a third stage of:

3. extracting residual salts and aqueous foreign-phase fractions with water from the organic reaction mixture I remaining after the second prepurification stage, before passing the remaining organic reaction mixture I to the separation zone comprising further rectification units.

2. A process as claimed in claim 1, wherein water saturated with n-butanol is the extracting agent in the first, third or first and third prepurification stage.

3. A process as claimed in claim 1, wherein the water added in the third prepurification stage is acidified in such a way that the aqueous phase has a ph of $\leq 6$ after the extraction.

4. A process as claimed in claim 1, wherein from 0.05 to 1 part by weight of water is added per part by weight of organic phase in the third prepurification stage.

5. A process as claimed in claim 1, wherein the residual reaction mixture I and the water in the third prepurification stage are mixed in a stirred kettle.

6. A process as claimed in claim 1, wherein the reaction mixture in a reaction kettle is stirred by a power of stirring ranging from 0.1 to 20.8 kW/m$^3$.

7. A process as claimed in claim 1, wherein said residence time of the reactants in a stirred reaction kettle ranges from 5 to 60 min.

8. A process as claimed in claim 1, wherein the wherein the internals in all rectification units are dual-flow trays and/or structured packings.

9. A process as claimed in claim 3, wherein the water added in the third prepurification stage is acidified such that the aqueous phase has a pH of 3 to 6 after the extraction.

10. A process as claimed in claim 4, wherein from 0.1 to 0.5 part by weight of water is added per part by weight of organic phase in the third prepurification stage.

11. A process as claimed in claim 6, wherein the reaction mixture in a reaction kettle is stirred by a power of stirring ranging from 0.5 to 1 kW/m$^3$.

12. A process as claimed in claim 7, wherein said residence time in a stirred reaction kettle ranges from 10 to 30 min.

13. A process as claimed in claim 5, wherein the residual reaction mixture I and the water in the third prepurification stage are mixed in a stirred kettle equipped with a single stage or multistage impeller stirrer.

14. A process as claimed in claim 2, wherein water saturated with n-butazol is process water from the esterification reaction.

* * * * *